US 9,515,159 B2

(12) United States Patent
Bischopink et al.

(10) Patent No.: US 9,515,159 B2
(45) Date of Patent: Dec. 6, 2016

(54) ELECTRONIC SENSOR APPARATUS FOR DETECTING CHEMICAL OR BIOLOGICAL SPECIES, MICROFLUIDIC APPARATUS COMPRISING SUCH A SENSOR APPARATUS, AND METHOD FOR PRODUCING THE SENSOR APPARATUS AND METHOD FOR PRODUCING THE MICROFLUIDIC APPARATUS (71) Applicant: Robert Bosch GmbH, Stuttgart (DE)

(72) Inventors: Georg Bischopink, Pliezhausen (DE); Franz Laermer, Weil Der Stadt (DE); Christian Dorrer, Stuttgart (DE); Thomas Brettschneider, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 169 days.

(21) Appl. No.: 14/021,350

(22) Filed: Sep. 9, 2013

(65) Prior Publication Data
US 2014/0077315 A1 Mar. 20, 2014

(30) Foreign Application Priority Data

Sep. 17, 2012 (DE) .................. 10 2012 216 497

(51) Int. Cl.
*H01L 29/66* (2006.01)
*H01L 21/02* (2006.01)
(Continued)

(52) U.S. Cl.
CPC ......... *H01L 29/66* (2013.01); *B01L 3/502707* (2013.01); *C12Q 1/6825* (2013.01);
(Continued)

(58) Field of Classification Search
CPC ........ H01L 29/66; H01L 21/02; C12Q 1/6825;
B01L 3/00; G01N 27/07; G01N 27/226;
G01N 33/5438; G01N 27/4145; G01N
27/3275; A61B 5/0002; G01D 9/005
(Continued)

(56) References Cited

U.S. PATENT DOCUMENTS 5,151,110 A * 9/1992 Bein et al. ...................... 95/140
7,776,794 B2   8/2010 Szaro et al.
(Continued)

FOREIGN PATENT DOCUMENTS

DE   101 22 133 A1   1/2002
DE   101 11 458 A1   9/2002
(Continued)

OTHER PUBLICATIONS

Braun T et al, "Large Area Embedding for Heterogenous System Integration", Electronic Components and Technology Conference (ECTC), 2010 Proceedings 60th, IEEE, Piscataway, NJ, USA, Jun. 1, 2010, p. 550-556, XP031694139.

Primary Examiner — David Vu
Assistant Examiner — Mouloucoulaye Inoussa
(74) Attorney, Agent, or Firm — Maginot, Moore & Beck LLP (57) ABSTRACT An electronic sensor apparatus for detecting chemical or biological species includes a semiconductor chip, a sensor device, and a substrate. The chip is produced from a semiconductor substrate and is configured for one or more functions such as: amplifying and/or evaluating an electrical voltage, amplifying and/or evaluating an electric current, amplifying and/or evaluating an electrical charge, and amplifying and/or reading out capacitance changes. The sensor device has an active surface configured to detect chemical or biological species and generate an electrical signal based on a species-characteristic interaction with the active surface. The electrical signal can be an electrical (Continued)

voltage, an electric current, an electrical charge and/or a capacitance change. The substrate is produced from a melt-moldable material and has a surface including first and second regions. The chip is at least partly embedded in the first region, and the sensor device is at least partly embedded in the second region.

15 Claims, 3 Drawing Sheets

(51) Int. Cl.
    *G01N 33/543* (2006.01)
    *C12Q 1/68* (2006.01)
    *B01L 3/00* (2006.01)

(52) U.S. Cl.
    CPC ......... *G01N 33/5438* (2013.01); *H01L 21/02* (2013.01); *B01L 2200/10* (2013.01); *B01L 2300/0636* (2013.01); *B01L 2300/0645* (2013.01); *B01L 2300/0816* (2013.01); *B01L 2300/0877* (2013.01)

(58) Field of Classification Search
    USPC .......................................... 257/414
    See application file for complete search history.

(56) References Cited

U.S. PATENT DOCUMENTS

| | | | |
|---|---|---|---|
| 2004/0000713 A1* | 1/2004 | Yamashita | A61B 5/0002 257/728 |
| 2004/0200734 A1 | 10/2004 | Co et al. | |
| 2006/0010964 A1* | 1/2006 | Sparks et al. | 73/54.01 |
| 2007/0122314 A1* | 5/2007 | Strand | B01J 19/0093 422/400 |

FOREIGN PATENT DOCUMENTS

| | | |
|---|---|---|
| EP | 1 591 780 A2 | 11/2005 |
| EP | 2 378 559 A1 | 10/2011 |
| KR | 10-2010-0100083 A | 9/2010 |
| WO | 2009/014390 A2 | 1/2009 |
| WO | 2010/089226 A1 | 8/2010 |

\* cited by examiner

ELECTRONIC SENSOR APPARATUS FOR DETECTING CHEMICAL OR BIOLOGICAL SPECIES, MICROFLUIDIC APPARATUS COMPRISING SUCH A SENSOR APPARATUS, AND METHOD FOR PRODUCING THE SENSOR APPARATUS AND METHOD FOR PRODUCING THE MICROFLUIDIC APPARATUS

This application claims priority under 35 U.S.C. §119 to patent application no. 10 2012 216 497.9, filed on Sep. 17, 2012 in Germany, the disclosure of which is incorporated herein by reference in its entirety.

BACKGROUND

The disclosure relates to an electronic sensor apparatus for detecting technical or biological species, a microfluidic apparatus comprising such a sensor apparatus, a method for producing such a sensor apparatus and a method for producing such a microfluidic apparatus.

Chemo- and biosensors are known in which a field effect transistor is realized on a silicon substrate, the gate of said transistor forming a detection electrode of the sensor, as disclosed for example in KR 10 2010 00100083 A and EP 2 378 559 A1.

Chemo- and/or biosensors are also known in which an electrode composed of gold is deposited on a silicon substrate, as disclosed for example in U.S. Pat. No. 7,776,794 B2.

Microfluidic systems constructed as polymeric multilayer arrangements and comprising chemo- and/or biosensors integrated therein are likewise known, as disclosed for example in US 2007/0122314 A1.

US 2004/0200734 A1 discloses a sensor for detecting biomolecules, for example proteins, nucleic acids or antibodies. The sensor comprises nanotubes which are connected to two electrodes and integrated into a microfluidic system, and biomolecules immobilized in the nanotubes. This sensor minimizes the reagent volume and enables rapid screening with a high throughput of potentially effective medicament compounds.

WO 2009/014390 A2 discloses a microfluidic sensor construction for the quantitative analysis of samples, such as, for instance, myoglobin and antibiotics. The construction comprises a lower plate, a middle plate and an upper plate. A reference electrode, a working electrode and an electrode connection are formed on the lower plate. The middle plate is placed onto the lower plate and comprises a sample inlet channel, a microfluidic channel passage which extends from the sample inlet channel and which serves as a guide for the sample flow over the entire middle plate and which branches into two partial channels at a position in the vicinity of the sample inlet channel. An enzyme conjugate reservoir is provided in one partial channel and a substrate reservoir is provided in the other branch. The two partial channels converge upstream of a detection channel, in the region of which the reference electrode and the working electrode are exposed on the first plate. The middle plate furthermore has a mixing channel, which is arranged at a position of the convergence downstream of the substrate reservoir and which has an air outlet channel, such that a sample which flows through the substrate reservoir reaches the detection channel later than a sample which flows through the enzyme conjugate reservoir. Finally, the middle plate also has an absorption channel, in which the sample fluid flowing out from the detection channel is absorbed, and an air inlet channel, which opens into an end of the absorption channel.

SUMMARY

The disclosure provides an electronic sensor apparatus for detecting chemical or biological species comprising the features described below, a microfluidic apparatus comprising such a sensor apparatus comprising the features described below, a method for producing such a sensor apparatus comprising the features described below, and a method for producing the microfluidic apparatus comprising the features described below. Advantageous embodiments of the sensor apparatus and of the microfluidic apparatus are subjects of the below description.

A first aspect of the disclosure provides an electronic sensor apparatus for detecting chemical or biological species, in particular ions, molecules, proteins, RNA molecules, DNA sequences, antigens, viruses, bacteria or cells. The electronic sensor apparatus comprises at least one semiconductor chip which is produced from a semiconductor substrate and is configured for one or more functions selected from a group comprising the following: amplifying and/or evaluating an electrical voltage, amplifying and/or evaluating an electric current, amplifying and/or evaluating an electrical charge and amplifying and/or reading out capacitance changes, at least one sensor device having an active sensor surface which is configured to detect chemical or biological species and to generate an electrical signal on account of a species-characteristic interaction with the active sensor surface, said electrical signal being selected from a group comprising the following: an electrical voltage, an electric current, an electrical charge and a capacitance change, and a substrate produced from a melt-moldable material and having a substrate surface comprising at least one first region and at least one second region, wherein the at least one semiconductor chip is applied or at least partly embedded in the at least one first region, and wherein the at least one sensor device is applied or at least partly embedded in the at least one second region.

The semiconductor chip can be embodied as an application-specific circuit, and it can comprise a microcontroller for controlling the functions embodied on the semiconductor chip.

The sensor device having the active sensor surface can be embodied as an electrode.

The electronic sensor apparatus according to the disclosure can be used to detect the presence of predetermined chemical or biological species in a surrounding solution and to measure the concentration thereof. One aspect of the electronic sensor apparatus according to the disclosure is that the sensor device are not situated on a semiconductor chip, but rather on a substrate produced from a melt-moldable material, referred to as "package" by a person skilled in the art.

At least the following advantages can be achieved with the electronic sensor apparatus:

Semiconductor-based electrical components (e.g. ICs of CMOS configuration) are usually produced on semiconductor wafers and subsequently singulated. In order to make electrical contact with the components and protect them, they are subsequently connected to a printed circuit board or some other carrier (e.g. a leadframe) for example by wire or metal bonds and are potted with a melt-moldable material (also called molding compound herein). In contrast thereto, during the production of an electronic sensor apparatus according to the disclosure, the semiconductor chip and the sensor device (e.g. the electrode) can be arranged on a wafer composed of molding compound in large numbers for parallel further processing. Accordingly, the electrical contact-making is not effected for individual components, but rather in parallel processing on the wafer surface simultaneously for a plurality of components.

Owing to the measure that the sensor device is not situated on the semiconductor chip, semiconductor surface area is saved and the semiconductor chip can be produced more cost-effectively. In particular, larger sensor devices can also be realized cost-effectively.

The sensor devices (e.g. the electrodes) can be positioned on the substrate surface of the substrate produced from the melt-moldable material and be dimensioned such that they can be functionalized by means of customary printing methods, such as, for instance, dot matrix printing or inkjet printing.

If the sensor devices are arranged on the substrate surface produced from the melt-moldable material in a manner closely adjacent to the semiconductor chip, then signal amplification of the signal effected at the sensor surface of the sensor device can be realized on the semiconductor chip, i.e. in direct proximity to the sensor device. As a result, long lines, cables or bonding wires can be avoided between the electrode on the sensor surface and the amplifier on the semiconductor chip and even very small signal changes can be detected, which improves the sensitivity of the sensor.

On the substrate surface of the sensor device produced from the melt-moldable material, with the exception of the areas above the sensor surface of the sensor device and the required contact-making devices (described below), it is possible to apply a passivation layer as protective layer, thereby preventing contamination by the analyte, e.g. by contact between the analyte and the melt-moldable material.

A second aspect of the disclosure provides a microfluidic apparatus for detecting chemical or biological species, in particular ions, molecules, proteins, RNA molecules, DNA sequences, antigens, viruses, bacteria or cells, which can be fed to the apparatus in an analyte solution. The microfluidic apparatus comprises at least one sensor apparatus in accordance with the first aspect of the disclosure. The same advantages mentioned above as for the electronic sensor apparatus in accordance with the first aspect of the disclosure can be achieved with the microfluidic apparatus.

A third aspect of the disclosure provides a method for producing an electronic sensor apparatus for detecting chemical or biological species, in particular ions, molecules, proteins, RNA molecules, DNA sequences, antigens, viruses, bacteria or cells. This method comprises the following steps:

applying or at least partly embedding a prefabricated semiconductor chip on or in a first region of a substrate surface of a substrate produced from a melt-moldable material, and applying or at least partly embedding a prefabricated sensor device on or in a second region of the substrate surface of the substrate produced from the melt-moldable material.

A fourth aspect of the disclosure provides a method for producing a microfluidic apparatus in accordance with the second aspect comprising an electronic sensor apparatus in accordance with the first aspect. This method comprises the following steps:

providing a first polymer substrate having a structurable surface and forming a cutout in said surface, arranging the electronic sensor apparatus in the cutout, providing a second polymer substrate having a structurable surface and forming a flow cell, in particular a channel, in said surface, placing the second polymer substrate onto the first polymer substrate, wherein the structured surface of the second polymer substrate faces the structured surface of the first polymer substrate and the flow cell of the second polymer substrate is arranged in a manner adjacent to the cutout, in particular the electronic sensor apparatus arranged therein, and areally connecting the structured surface of the second polymer substrate to the structured surface of the first polymer substrate at least in regions outside the cutout of the first polymer substrate.

In the sensor apparatus in accordance with the first aspect of the disclosure, the first region and the second region of the substrate surface can be embodied in a manner spaced apart from one another, in particular in a manner not overlapping one another. As a result, the semiconductor chip and the sensor device can be arranged in the substrate produced from the melt-moldable material such that the surface of the composite assembly comprising the semiconductor chip and the sensor device with the substrate has no appreciable topography. This in turn simplifies the integration of the sensor apparatus into a microfluidic apparatus. In particular, the sensor devices (e.g. the electrodes) are then in direct contact with a flow in a channel leading along the active sensor surface.

At least one conductive connection between the sensor device in the second region and the semiconductor chip in the first region can be applied or at least partly embedded on the substrate surface. The conductive connection may have been applied on the substrate produced from a melt-moldable material by means of a thin-film technology or by means of a printing method. Suitable printing methods include, for example, screen printing, dot matrix printing or inkjet printing. Through the use of a printing method, the production of the conductive connection is cost-effective and relatively simple in terms of process engineering.

The substrate surface can comprise at least one third region in which at least one contact-making layer is applied or at least partly embedded. Furthermore, at least one conductive connection between the contact-making layer and the semiconductor chip can be applied or at least partly embedded on the substrate surface. This conductive connection may have been applied on the substrate produced from a melt-moldable material likewise by means of a thin-film technology or by means of a printing method, such as dot matrix printing or inkjet printing, for instance. As a result, the production of the conductive connection is cost-effective and relatively simple in terms of process engineering.

The melt-moldable material (molding compound) used can be an epoxy-based filling compound preferably interspersed with fillers, such as glass beads or glass fibers, for instance, in order to adapt the coefficient of thermal expansion to that of the semiconductor.

The conductive compounds formed on the substrate surface of the melt-moldable material can be produced from an electrically conductive material, in particular from a metal, for example copper, aluminum, silver or gold, or from electrically conductive inks developed for screen printing and inkjet printing techniques, or from pastes on the basis of silver, for example.

The sensor device (e.g. the electrode) can also be produced from the electrically conductive materials mentioned above. A contact-connection of the sensor device (e.g. of the electrode) may likewise have been produced from said electrically conductive materials.

A coating can be applied on the active sensor surface, said coating being configured to selectively detect a specific chemical or biological species or groups of species upon contact with an analyte solution. The coating applied on the active sensor surface can comprise at least one layer selected from a group comprising the following: a layer comprising at least one catcher molecule which is immobilized in particular with at least one connecting molecule (also called linker molecule) on or at said layer, a layer which is functionalized with at least one DNA sequence and/or at least one antibody, and an ion-selective layer. This functionalization of the active sensor surface can be performed before the singulation of the sensor apparatuses at the wafer level, as a result of which this process step can be implemented very cost-effectively.

The microfluidic apparatus in accordance with the second aspect of the disclosure can comprise a first polymer substrate having a structured surface having at least one cutout in which the electronic sensor apparatus is accommodated in an at least partly embedded manner. Furthermore, the microfluidic apparatus can comprise a second polymer substrate having the following: a structured surface having at least one flow cell, in particular a channel, formed therein, which is configured to guide an analyte solution and to feed it to the electronic sensor apparatus, an inflow line, which opens in a first end section of the flow cell and which is configured to guide the analyte solution into the flow cell, and an outflow line, which opens in a second end section of the flow cell and which is configured to discharge a residual solution from the flow cell. A microfluidic apparatus embodied in this way comprises only two structured polymer substrates as essential components that guide the microfluidic flow, and is therefore relatively simple and cost-effective to produce.

The inflow line and/or the outflow line can open in that surface of the second polymer substrate which is situated opposite the structured surface of the second polymer substrate. Thus, the openings of the inflow line and of the outflow line are arranged on a relatively large surface and can be reached in an easily accessible manner.

The functional surface of the sensor device of the sensor apparatus can be oriented such that its surface normal points out of the cutout, that the structured surface of the second polymer substrate faces the structured surface of the first polymer substrate, and that the flow cell is arranged in the second polymer substrate in a manner adjacent to the cutout in the first polymer substrate, in particular adjacent to the functional surface of the sensor layer or of the sensor substrate of the sensor apparatus. By virtue of this configuration of the polymer substrates, the latter, during the assembly of the microfluidic apparatus, merely need to be placed one on top of the other in a manner facing one another with register accuracy and to be connected to one another, which simplifies assembly.

The microfluidic apparatus can comprise a structured adhesive film which can be arranged in a sandwich-like manner between the structured surface of the first polymer substrate and the structured surface of the second polymer substrate. By virtue of the adhesive film, the connection between the first and second polymer substrates can be implemented simply and cost-effectively.

The first and second polymer substrates can be produced from a thermoplastic, for example from PC (polycarbonate), PP (polypropylene), PE (polyethylene), PMMA (polymethyl methacrylate), COP (cycloolefin polymer) or COC (cycloolefin copolymer).

The microfluidic apparatus can furthermore comprise a cover layer, in particular a cover film, which is arranged on that surface of the second polymer substrate which is situated opposite the structured surface of the second polymer substrate. The cover layer protects the openings of the inflow line and of the outflow line against the ingress of impurities.

In the method in accordance with the third aspect, the first region and the second region of the substrate surface can be arranged in a manner offset from one another, in particular in a manner not overlapping one another. As already mentioned above, as a result, the semiconductor chip and the sensor layer or the sensor substrate can be arranged in the substrate produced from the melt-moldable material such that the surface of the composite assembly comprising the semiconductor chip and the sensor layer or the sensor substrate with the substrate has no appreciable topography, which in turn simplifies the integration of the sensor apparatus into a microfluidic apparatus.

In order to produce a multiplicity of such electronic sensor apparatuses in a parallel processing production process, a multiplicity of prefabricated semiconductor chips can be positioned on an adhesive film, wherein the surface of the semiconductor chip faces the adhesive film. The semiconductor chips positioned on the adhesive film can then be encapsulated by injection molding with a melt-moldable material (molding compound) and can be embedded into the melt-moldable material in this way. Afterward, the adhesive film can be removed. A substrate composed of melt-moldable material with a multiplicity of semiconductor chips embedded therein can thus be obtained.

In the method in accordance with the third aspect of the disclosure, furthermore, at least one electrically conductive connection between the sensor layer or the sensor substrate and the semiconductor chip can be formed on the substrate surface of the substrate produced from the melt-moldable material. Moreover, in this method, a contact-making layer can be applied or at least partly embedded in a third region of the substrate surface of the substrate produced from the melt-moldable material. Furthermore, at least one electrically conductive connection between the contact-making layer and the semiconductor chip can be formed on the substrate surface of the substrate produced from the melt-moldable material. As already mentioned above, these conductive connections can be applied by means of a printing method cost-effectively and relatively simply in terms of process engineering.

BRIEF DESCRIPTION OF THE DRAWINGS

The disclosure is described in further detail below by way of example on the basis of embodiments of the electronic sensor and of the microfluidic apparatus according to the disclosure and embodiments of methods for producing them, these embodiments being described on the basis of the accompanying figures, in which.

DETAILED DESCRIPTION

Figure 1:
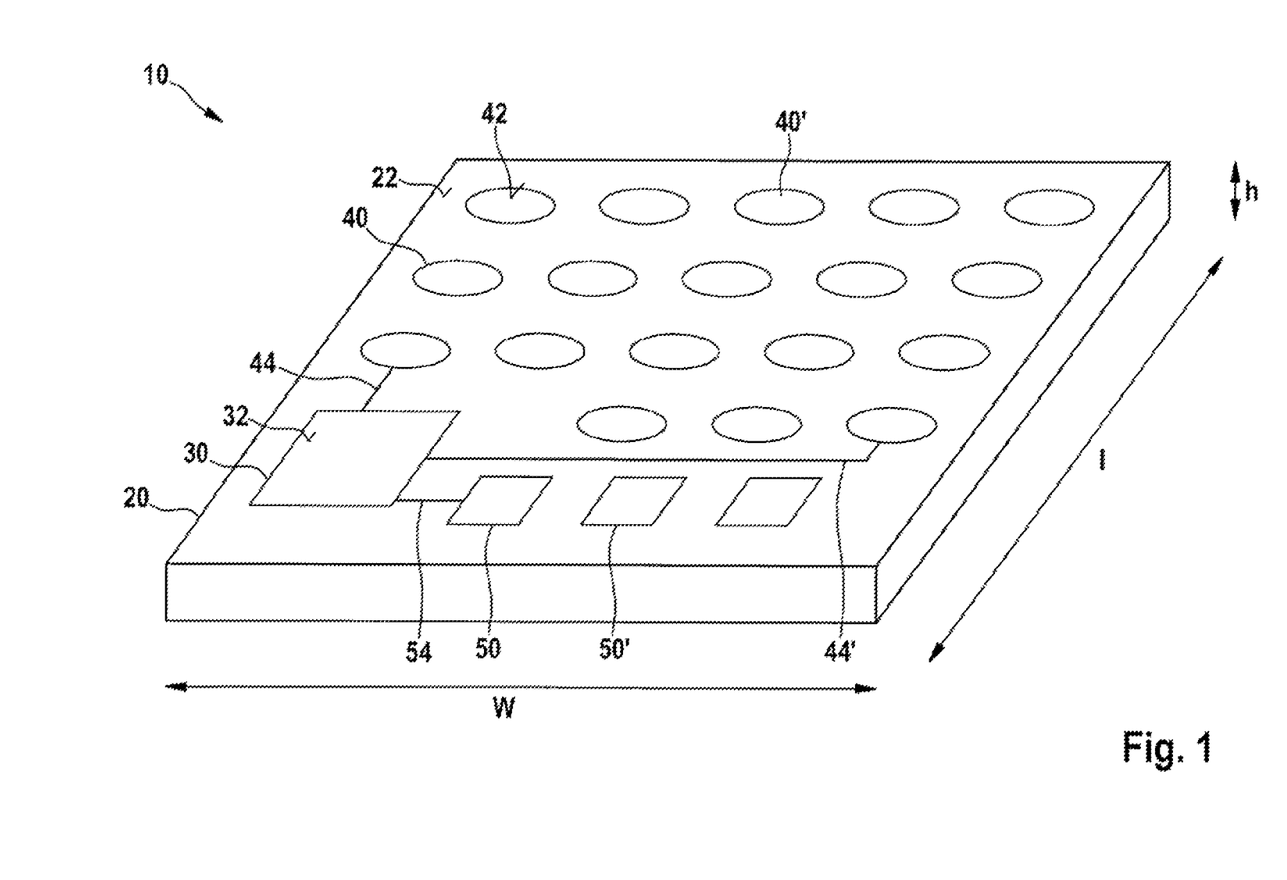
FIG. 1 shows a schematic perspective view of an embodiment of an electronic sensor apparatus in accordance with the first aspect of the disclosure.

In the embodiment of an electronic sensor apparatus 10 as shown in FIG. 1, this apparatus comprises a substrate 20 produced from a melt-moldable material (molding compound) and having a substrate surface 22, a semiconductor chip 30 (also see FIG. 2, lower illustration) produced beforehand from a silicon substrate 36 and applied, embedded or at least partly embedded in a first region of the substrate surface 22, a multiplicity of sensor devices 40, 40' applied, embedded or at least partly embedded in a multiplicity of corresponding respective second regions on the substrate surface 22, a corresponding multiplicity of electrically conductive connections 44, 44' applied on the substrate surface 22 and forming an electrically conductive connection between a respective sensor device 40, 44 and the semiconductor chip 30. The electronic sensor apparatus 10 furthermore comprises a multiplicity of contact-making layers 50, 50' applied or at least partly embedded in respective third regions on the substrate surface 22, and a corresponding multiplicity of conductive connections 54 applied or at least partly embedded on the substrate surface 22 and forming an electrically conductive connection between a respective contact-making layer 50, 50' and the semiconductor chip 30.

The semiconductor chip 30 was prefabricated using production processes known from the field of semiconductor technology. The semiconductor chip 30 comprises at least one device for amplifying voltages, currents, electrical charges and/or for reading out capacitance changes which can be produced in one of the sensor devices 40, 40' during use owing to a detection of a chemical or biological species 12, 12', 12" (see FIG. 2, upper illustration) in the sensor device 40, 40'. The semiconductor chip 30 furthermore comprises a microcontroller for controlling the amplifying device(s). The semiconductor chip 30 is embodied as an application-specific integrated circuit (ASIC).

The other electrical elements 40, 40', 44, 50, 50', 54 are produced or applied to the substrate surface 22 of the melt-moldable material (molding compound) using thin-film technologies or by means of printing methods, for example screen printing, dot matrix printing or inkjet methods. In order to simplify the illustration, FIG. 1 does not show all electrically conductive connections 44 proceeding from the semiconductor chip 30 and leading to the respective sensor devices 40, 40', nor all electrically conductive connections 54 proceeding from the semiconductor chip 30 and leading to the respective contact-making layers 50, 50'.

The sensor devices (e.g. electrodes) 40, 40' each have an active sensor surface 42, on which is applied a coating that allows detection selectively of specific chemical or biological species 12, 12', 12", such as, for instance, ions, molecules, proteins, RNA molecules, DNA sequences, antigens, viruses, bacteria or cells, upon contact with an analyte solution. For this purpose, in one embodiment, specific catcher molecules 46, such as antibodies or DNA fragments, for instance, were applied on the active sensor surfaces 42 and were immobilized on the active sensor surface 42, if appropriate, for example by means of suitable connecting molecules 48 (also designated as linkers or linker modules by a person skilled in the art). In an alternative embodiment to this, an ion-selective layer can also be applied on the active sensor surface 42, see FIG. 2, upper illustration (excerpt enlargement).

Figure 2:
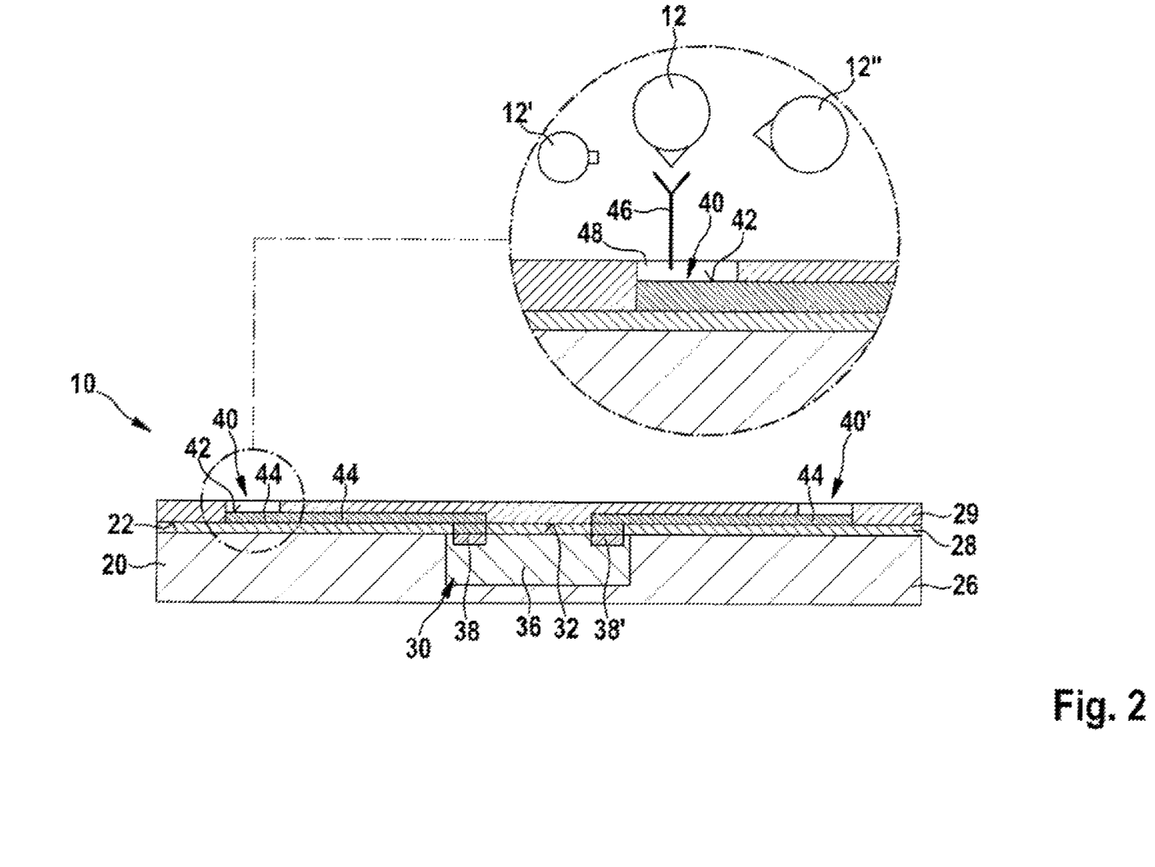
FIG. 2 shows a schematic cross-sectional view of the electronic sensor apparatus from FIG. 1 and a detail enlargement of this cross-sectional view.

FIG. 2 shows a singulated electronic sensor apparatus 10 in cross section. In order to produce a multiplicity of such electronic sensor apparatuses 10 in a parallel processing production process, a multiplicity of prefabricated semiconductor chips 30 were positioned on an adhesive film (not shown), wherein the chip surface 32 faces the adhesive film, and were encapsulated by injection molding with a melt-moldable material (molding compound) and embedded into the melt-moldable material 26 in this way. Afterward, the adhesive film was removed, such that a substrate composed of melt-moldable material 26 with a multiplicity of semiconductor chips 30 embedded therein is obtained. A first photoresist as photoresist passivation layer 28 was applied on this molding compound substrate and subsequently opened above predetermined contact areas 38, 38' on the chip surfaces 32 of the semiconductor chips 30. The electrically conductive connections 44, 44' and the sensor devices 40, 40' electrically conductively connected thereby to the semiconductor chips 30, which sensor devices can be embodied as electrodes, are then produced on the photoresist passivation layer 28.

In order to produce the electrically conductive connections 44, 44' and/or the sensor devices 40, 40', it is possible to use electrolytic methods and thus to apply electrically conductive materials, in particular metals, for example copper, aluminum, silver or gold.

The electrically conductive connections 54 and the contact-making layers 50, 50' electrically conductively connected thereby to the semiconductor chips 30 are applied on the photoresist passivation layer 28. Electrolytic methods can likewise be used for this purpose.

A second photoresist as photoresist stop layer 29 is then applied. This stop layer 29 is opened only above the sensor devices 40, 40', i.e. in the second regions, and above the contact-making layers 50, 50'.

The sensor devices 40, 40' and/or the contact-making layers 50, 50' are covered with respective further layers in subsequent processes. By way of example, the contact-making areas 50, 50' can be covered with gold. In particular, the sensor devices 40, 40' are covered with the coating that allows detection selectively of specific chemical or biological species 12, 12', 12" upon contact with an analyte solution. In this case, different sensor devices 40, 40' or groups of sensor devices can be functionalized with different coatings suitable for detecting different predetermined chemical or biological species, such that different chemical or biological species can be detected by means of the differently functionalized sensor devices 40, 40'.

Figure 3:
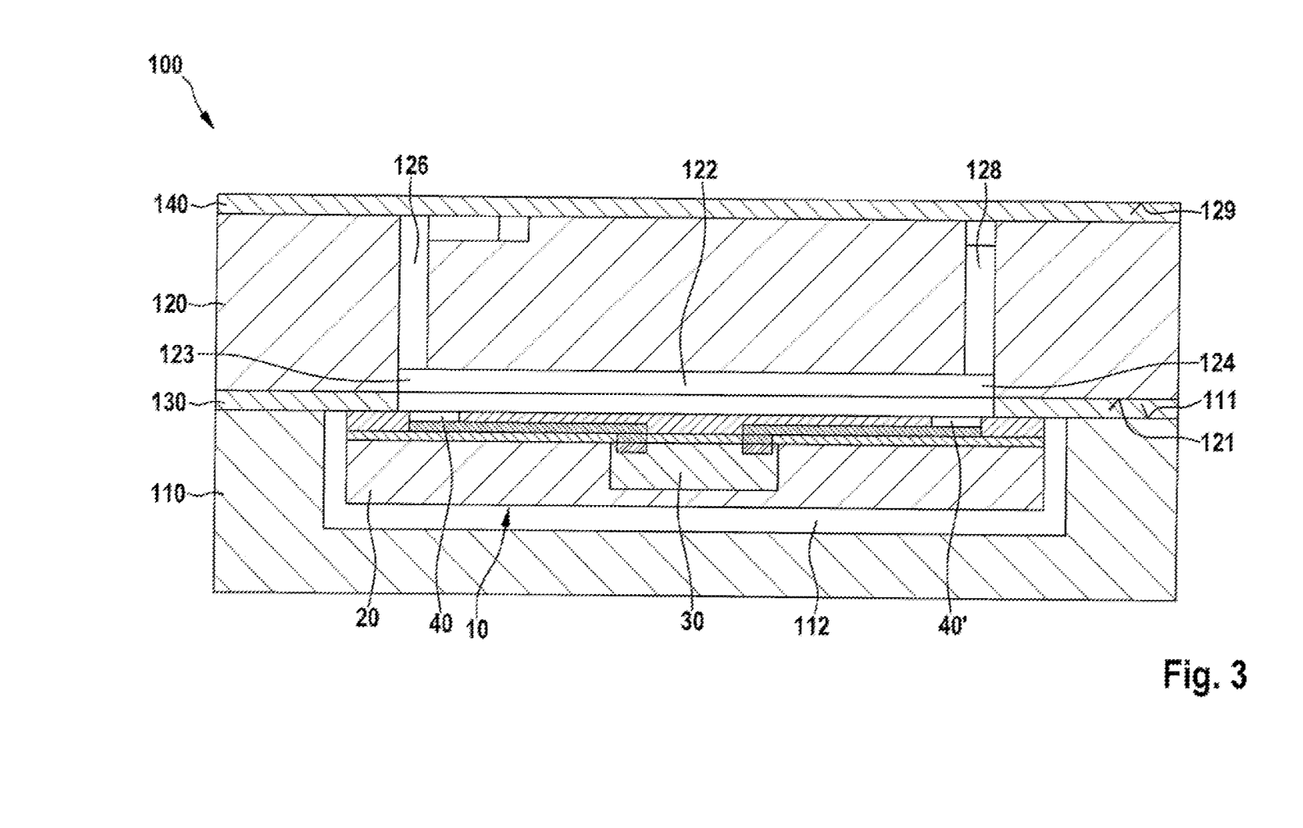
FIG. 3 shows a schematic cross-sectional view of an embodiment of a microfluidic apparatus in accordance with the second aspect of the disclosure, in which the sensor apparatus from FIG. 1 is integrated.

FIG. 3 shows an embodiment of the integration of an electronic sensor apparatus 10 from FIG. 1 into a microfluidic apparatus 100. The latter comprises a multilayered construction having two structured polymer substrates 110, 120.

The first (in FIG. 3 lower) polymer substrate 110 has a structured surface 111, in which a cutout 112 is formed. An electronic sensor apparatus 10 is accommodated in said cutout 112 such that the upper surface of the electronic sensor apparatus 10 is arranged flush with the surface 111 of the first polymer substrate 110 in the regions outside the cutout 112.

The second (in FIG. 3 upper) polymer substrate 120 has a structured or structurable surface 121 facing the first polymer substrate 110. In the surface 121, a flow cell 122 is formed, for example a channel extending in the region of the sensor devices 40, 40' of the electronic sensor device 10 embedded in the cutout 112 in the first polymer substrate 110. The flow cell 122 or the channel is assigned an inflow line 126 for feeding an analyte and/or a washing solution. In this case, the inflow line 126 opens in a first end section 123 of the flow cell 122. The flow cell 122 or the channel is also assigned an outflow line 128 for discharging the analytes and/or the washing solution. The outflow line 128 opens in a second end section 124 of the flow cell 122 or of the channel.

The electronic sensor apparatus 10 is areally connected to the second polymer substrate in regions outside the flow cell 122. The second (in FIG. 3 upper) polymer substrate 120 is areally connected to the first (in FIG. 3 lower) polymer substrate 110 in regions outside the cutout 112 in the surface 111 of the first polymer substrate 110. A structured adhesive film 130, for example a hotmelt adhesive film, is provided for the areal connection. The adhesive film 130 brings about the areal connection of the electronic sensor apparatus 10 to the second polymer substrate 120 in the region outside the flow cell 122 and the areal connection between the second polymer substrate 120 and the first polymer substrate 110 in the region outside the cutout 112.

As an alternative to the connection by means of the adhesive film 130, these connections or the areal connection can also be brought about by welding, for instance by thermocompression welding or laser welding.

On a surface 129 of the second polymer substrate 120 that faces away from the structured surface 121, a cover layer 140 is also applied for protecting the entrances of the inflow line 126 and of the outflow line 128. The cover layer 140 can be embodied as a further adhesive film or as a polymer plate.

In addition to the electronic sensor apparatus 10, the microfluidic apparatus 100 also comprises further microfluidic elements (not shown), such as, for instance, valves, pumps, chambers or mixing devices, which are required for loading, operating and cleaning the active surfaces of the sensor apparatus 10.

For the electrical supply of the electronic sensor apparatus 10 integrated into the microfluidic apparatus 100, the sensor apparatus 10, in particular by means of the contact-making layers 50, 50' thereof, for example by means of spring contact pins (not shown) or the contact devices (not shown) that are identically functional, is contact-connected to conductor tracks or metal or wire bonds (not shown) integrated in the microfluidic apparatus.

The electronic sensor apparatus 10 or the microfluidic apparatus 100 equipped therewith can be used in analytical systems, in particular for microfluidic lab-on-chip systems, for environmental analysis or medical diagnostics.

Although the embodiments described above use a silicon substrate as semiconductor chip, the disclosure is not restricted thereto, but rather is applicable to any semiconductor chips.

LIST OF REFERENCE SIGNS

10 Sensor apparatus
12, 12', 12" Chemical or biological species
20 Substrate
22 Substrate surface
26 Melt-moldable material
28 Photoresist passivation layer
29 Photoresist stop layer
w Width of the substrate
l Length of the substrate
h Thickness of the substrate
30 Semiconductor chip
32 Semiconductor chip surface
36 Semiconductor substrate
38, 38' Contact area
40, 40' Sensor device
42 Active sensor surface
44, 44' Electrically conductive connection
46 Catcher molecule
48 Linker molecule
50, 50' Contact-making layer
54 Electrically conductive connection
100 Microfluidic apparatus
110 First polymer substrate
111 Structured or structurable surface
112 Cutout
120 Second polymer substrate
121 Structured or structurable surface
122 Flow cell
123 First end section
124 Second end section
126 Inflow line
128 Outflow line
129 Surface
130 Adhesive film

What is claimed is:

1. An electronic sensor apparatus for detecting chemical or biological species, comprising:
    a substrate produced from a melt-moldable material and having a first upper surface region and a second upper surface region;
    a sensor device supported by the first upper surface region and having an active sensor surface configured to detect chemical or biological species and to generate an electrical signal on account of a species-characteristic interaction with the active sensor surface, said electrical signal being selected from a group including: an electrical voltage, an electric current, an electrical charge and a capacitance change;
    a semiconductor chip produced from a semiconductor substrate and supported by the second upper surface region, the at least one semiconductor chip configured to perform one or more functions selected from a group including: amplifying and/or evaluating an electrical voltage, amplifying and/or evaluating an electric current, amplifying and/or evaluating an electrical charge, and amplifying and/or reading out capacitance changes; and
    a conductive connection extending along the first upper surface region and the second upper surface region, and connecting the sensor device to the semiconductor chip.

2. The sensor apparatus according to claim 1, wherein the first upper surface region and the second upper surface region are spaced apart from one another.

3. The sensor apparatus according to claim 1, wherein the conductive connection between the sensor device and the semiconductor chip extends along a photo-resist passivation layer on an uppermost surface of the substrate.

4. The sensor apparatus according to claim 1, wherein:
    the substrate surface includes at least one third upper surface region in which at least one contact-making layer is supported; and
    at least one conductive connection between the at least one contact-making layer and the at least one semiconductor chip is supported on the uppermost surface of the substrate.

5. The sensor apparatus according to claim 1, wherein a coating is applied on the active sensor surface, said coating configured to selectively detect a specific chemical or biological species or groups of species upon contact with an analyte solution.

6. The sensor apparatus according to claim 5, wherein the coating applied on the active sensor surface includes at least one layer selected from a group including: a layer comprising at least one catcher molecule immobilized on or at said layer, a layer which is functionalized with at least one DNA sequence and/or at least one antibody, and an ion-selective layer.

7. The electronic sensor apparatus according to claim 1, wherein the chemical or biological species are ions, molecules, proteins, RNA molecules, DNA sequences, antigens, viruses, bacteria or cells.

8. The electronic sensor apparatus according to claim 2, wherein the first upper surface region and the second upper surface region do not overlap one another.

9. The sensor apparatus according to claim 6, wherein:
the at least one layer comprises at least one catcher molecule immobilized on or at said layer; and
the at least one catcher molecule is immobilized on or at said layer with at least one connecting or linker molecule.

10. A microfluidic apparatus for detecting chemical or biological species which can be fed to the apparatus in an analyte solution, the microfluidic apparatus including at least one electronic sensor apparatus, comprising:
a substrate produced from a melt-moldable material and having a first upper surface region and a second upper surface region;
a sensor device supported by the first upper surface region and having an active sensor surface configured to detect chemical or biological species and to generate an electrical signal on account of a species-characteristic interaction with the active sensor surface, said electrical signal being selected from a group including: an electrical voltage, an electric current, an electrical charge and a capacitance change;
a semiconductor chip produced from a semiconductor substrate and supported by the second upper surface region, the at least one semiconductor chip configured to perform one or more functions selected from a group including: amplifying and/or evaluating an electrical voltage, amplifying and/or evaluating an electric current, amplifying and/or evaluating an electrical charge, and amplifying and/or reading out capacitance changes; and
a conductive connection extending along the first upper surface region and the second upper surface region, and connecting the sensor device to the semiconductor chip.

11. The microfluidic apparatus according to claim 10, further comprising:
a first polymer substrate having a structured surface having at least one cutout in which the at least one electronic sensor apparatus is accommodated in an at least partly embedded manner; and
a second polymer substrate, including:
a structured surface having at least one flow cell formed therein and configured to guide the analyte solution and feed the analyte solution to the at least one electronic sensor apparatus;
an inflow line configured to open in a first end section of the at least one flow cell and configured to guide the analyte solution into the at least one flow cell; and
an outflow line configured to open in a second end section of the at least one flow cell and configured to discharge a residual solution from the at least one flow cell.

12. The microfluidic apparatus according to claim 11, wherein:
a functional surface of a sensor layer or of a sensor substrate of the at least one electronic sensor apparatus is oriented such that its surface normal points out of the at least one cutout,
the structured surface of the second polymer substrate is configured to face the structured surface of the first polymer substrate, and
the at least one flow cell is arranged in the second polymer substrate in a manner adjacent to the at least one cutout in the first polymer substrate.

13. The microfluidic apparatus according to claim 11, further comprising: a structured adhesive film arranged in a sandwich-like manner between the structured surface of the first polymer substrate and the structured surface of the second polymer substrate.

14. The microfluidic apparatus according to claim 11, wherein the at least one flow cell is a channel.

15. The microfluidic apparatus according to claim 12, wherein the at least one flow cell is arranged adjacent to the functional surface of the sensor layer or sensor substrate of the sensor apparatus.

* * * * *